United States Patent [19]

Harley

[11] Patent Number: 5,246,903
[45] Date of Patent: * Sep. 21, 1993

[54] PROCESS AND CATALYST FOR THE DEHYDROHALOGENATION OF HALOGENATED HYDROCARBONS OR ALKYLENE HALOHYDRINS

[75] Inventor: A. Dale Harley, Baton Rouge, La.

[73] Assignee: The Dow Chemical Company, Midland, Mich.

[*] Notice: The portion of the term of this patent subsequent to Aug. 21, 2008 has been disclaimed.

[21] Appl. No.: 918,997

[22] Filed: Jul. 23, 1992

Related U.S. Application Data

[63] Continuation-in-part of Ser. No. 319,516, Mar. 6, 1989, abandoned, which is a continuation-in-part of Ser. No. 53,925, May 26, 1987, Pat. No. 4,816,609.

[51] Int. Cl.$^5$ .................... B01J 21/18; B01J 23/02; B01J 23/06
[52] U.S. Cl. .................... 502/183; 502/181; 502/226; 502/243; 502/342
[58] Field of Search ............ 502/181, 183, 226, 243, 502/342

[56] References Cited

U.S. PATENT DOCUMENTS

| 2,134,102 | 10/1938 | Cass | 570/226 |
|---|---|---|---|
| 2,322,258 | 6/1943 | Strosacker et al. | 570/226 |
| 2,323,226 | 6/1943 | Levine et al. | 570/226 |
| 2,415,294 | 2/1947 | Levine et al. | 570/226 |
| 2,765,349 | 10/1956 | Conrad | 570/226 |
| 2,803,678 | 8/1957 | Conrad | 570/226 |
| 2,803,679 | 8/1957 | Conrad | 570/226 |
| 3,230,181 | 1/1966 | Lestor | 570/226 |
| 3,244,758 | 4/1966 | Eberhardt | 585/320 |
| 3,325,554 | 6/1967 | Addy | 570/226 |
| 3,677,932 | 7/1972 | Hardesty et al. | 502/226 |
| 3,736,250 | 5/1973 | Berg et al. | 502/226 |
| 3,870,762 | 3/1975 | Stacey et al. | 570/226 |
| 3,909,451 | 9/1975 | Wihelm | 502/226 |
| 4,104,317 | 8/1978 | Antos | 502/226 |
| 4,144,192 | 3/1979 | Reinhardt, III | 570/226 |
| 4,225,519 | 9/1980 | Reinhardt, III | 570/226 |
| 4,309,279 | 1/1982 | Chester et al. | 208/120 |
| 4,929,783 | 5/1990 | Smith | 585/452 |
| 5,041,406 | 8/1991 | Harley et al. | 502/226 |

FOREIGN PATENT DOCUMENTS

| 146520 | 9/1983 | Japan . |
| 1197531 | 9/1986 | Japan . |
| 1197532 | 9/1986 | Japan . |
| 722892 | 3/1980 | U.S.S.R. . |
| 791792 | 3/1958 | United Kingdom . |
| 2008117 | 5/1979 | United Kingdom . |

OTHER PUBLICATIONS

Mochida, Isao et al. Langmuir, 4, pp. 626-630 (1988).
Venuto, P. B. et al., Catal. Rev.-Sci. Eng., 18(1), pp. 1-22 (1978).
Mochida, Isao et al., Applied Catalysis, 18, pp. 105-115 (1985).
Mochida, Isao et al. Chemistry Letters, pp. 833-836 (1985).
Mochida, Isao et al. Applied Catalysis, 32, pp. 37-44 (1987).

Primary Examiner—Patrick P. Garvin
Assistant Examiner—E. D. Irzinski

[57] ABSTRACT

An unsaturated halohydrocarbon such as vinylidene chloride is produced by the dehydrohalogenation of haloalkanes such as 1,1,1-trichloroethane or 1,1,2-trichloroethane, by contacting the haloalkane with a Group IA metal halide and a Group IIA or IIB metal oxide or metal hydroxide, together supported on a porous carrier material, under reaction conditions sufficient to form the corresponding unsaturated hydrocarbon and a Group IIA or IIB metal halide. The Group IIA or IIB metal oxide or metal hydroxide may be regenerated by contacting the Group IIA or IIB metal halide with an alkanol or water. In one embodiment, the process is initiated by contacting a novel catalyst comprising a Group IA metal cation such as Cs, a Group IIA or IIB metal cation such as Mg and a neutralizing number of halide anions such as chloride distributed on a support such as silica, with water or an alkanol under reaction conditions sufficient to form the Group IA metal halide and the Group IIA or IIB metal oxide or metal hydroxide supported on a porous carrier material. The process of the invention is also useful for the dehydrohalogenation of alkylene halohydrins to produce alkylene oxides. The process of the invention may be carried out in a riser reactor system, whereby the reactants are cycled in a continuous process.

8 Claims, No Drawings

PROCESS AND CATALYST FOR THE DEHYDROHALOGENATION OF HALOGENATED HYDROCARBONS OR ALKYLENE HALOHYDRINS

CROSS REFERENCE TO RELATED APPLICATIONS

The present application is a continuation-in-part of U.S. Ser. No. 07/319,516, filed Mar. 6, 1989, now abandoned, which was a continuation-in-part of U.S. Ser. No. 07/053,925, filed May 26, 1987, now U.S. Pat. No. 4,816,609.

BACKGROUND OF THE INVENTION

This invention relates to the dehydrohalogenation of halogenated hydrocarbons or alkylene halohydrins. More specifically, it pertains to a process and a catalyst for the dehydrohalogenation of halogenated hydrocarbons or alkylene halohydrins to produce the corresponding unsaturated halohydrocarbon, unsaturated hydrocarbon, or alkylene oxide.

Unsaturated halohydrocarbons, unsaturated hydrocarbons, and alkylene oxides are extremely useful for the preparation of various polymeric compositions. For example, 1,1-dichloroethene, commonly known as vinylidene chloride, can be used to produce vinylidene chloride polymers. Vinylidene chloride polymers have an extremely high barrier resistance to the transmission of oxygen and water vapors. Thus, such polymers, particularly copolymers of vinylidene chloride and vinyl chloride, acrylates or other monomers, are very useful as films or coatings in food packaging composites. Other copolymers produced from vinylidene chloride show excellent resistance to solvents and corrosive chemicals and have a high degree of abrasion resistance, toughness and dimensional stability. Such durable copolymers are extremely useful in rigid extrusions, tank linings, monofilaments, and paint and cement additives.

U.S. Pat. No. 3,984,489 describes a process for preparing vinylidene chloride by the caustic dehydrochlorination of 1,1,2-trichloroethane in the presence of an amine. This caustic cracking of a chlorinated hydrocarbon leads to the formation of a salt stream which leads to waste deposit problems and causes the loss of chlorine.

U.S. Pat. Nos. 2,765,349; 2,803,678 and 2,803,679 describe a dehydrochlorination process utilizing a metal salt or metal oxide as a catalyst. U.S. Pat. No. 3,230,181 describes a dehydrohalogenation process utilizing calcium bromide as a catalyst. United Kingdom patent application 2,008,117A describes the preparation of vinylidene chloride by the vapor phase dehydrochlorination of 1,1,2-trichloroethane in the presence of a cesium halide catalyst. U.S. Pat. Nos. 4,144,192 and 4,225,519 describe the dehydrochlorination of 1,1,2-trichloroethane in the presence of a cesium nitrate catalyst. U.S. Pat. No. 3,870,762 discloses a vapor phase dehydrochlorination process utilizing a chloride or fluoride of potassium, rubidium or cesium. Japanese patent applications Nos. 61-197531 and 61-197532 disclose the use of a cesium chloride catalyst in a dehydrochlorination process wherein the process is periodically interrupted and the catalyst is heated to 325° C. 550° C.

The above processes utilizing a catalyst suffer from deactivation of the catalyst due to the formation of coke on the catalyst surface. The formation of by-products and/or low selectivity to the desired products are also continuing problems in dehydrohalogenation reactions in general.

What is needed is an efficient dehydrohalogenation process that would avoid the waste disposal and halogen loss problems of prior methods by providing a means for safely and economically removing any salt or hydrogen halide produced by the dehydrohalogenation reaction. A process is also needed that would allow for the catalyst to be regenerated at lower process temperatures. A process is also needed that would provide for a high selectivity of the desired dehydrohalogenated product.

SUMMARY OF THE INVENTION

The present invention solves many of the aforementioned problems inherent in conventional dehydrohalogenation methods. In its first aspect, the invention relates to a dehydrohalogenation catalyst in the form of a compound comprising a Group IA metal cation, a Group IIA or IIB metal cation and a neutralizing number of counter anions supported on a porous carrier material. It has surprisingly been found that such a catalyst does not rapidly deactivate in typical dehydrohalogenation reactions when the catalyst is used in the presence of an alkanol and oxygen. The catalyst of the present invention also provides for high selectivity of the desired dehydrohalogenated product.

In a second aspect this invention relates to a dehydrohalogenation process which comprises contacting a halogenated hydrocarbon or alkylene halohydrin with a Group IA metal halide, and a Group IIA or IIB metal oxide or metal hydroxide, together supported on a porous carrier material, under reaction conditions sufficient to form a reaction product comprising a corresponding unsaturated halohydrocarbon, unsaturated hydrocarbon, or alkylene oxide.

In one preferred embodiment of this process, the reaction product further comprises a Group IIA or IIB metal halide, and the process further comprises the simultaneous step of contacting the Group IIA or IIB metal halide with a regenerant comprising an alkanol or water under reaction conditions sufficient to form a Group IIA or IIB metal oxide or metal hydroxide.

In a second preferred embodiment, the reaction product further comprises a Group IIA or IIB metal hydroxy halide, and the process further comprises the simultaneous step of heating the Group IIA or IIB metal hydroxy halide under reaction conditions sufficient to form a Group IIA or IIB metal oxide or metal hydroxide.

It has been discovered that this process is highly selective and provides for the capture of the halogen as it is removed from the halogenated hydrocarbon or alkylene halohydrin, thereby avoiding expensive waste of the halogen. The process of the present invention, when practiced in the presence of an oxygen source, also avoids deactivation of the catalyst due to coke formation on the catalyst surface.

Advantageously, these processes are highly selective, have a high catalytic capacity, and regenerate the catalytic material at relatively low optimum temperatures.

DETAILED DESCRIPTION OF ILLUSTRATIVE EMBODIMENTS

The catalyst of the present invention is advantageously a salt of a Group IA metal (alkali metal), a Group IIA or IIB metal and a neutralizing number of counter anions supported on a porous carrier material. Preferable Group IA metals include potassium, rubidium and cesium, with cesium being most preferred. Preferably, the Group IIA or IIB metals are Group IIA metals (alkaline earth metals) and more preferably are magnesium, calcium, strontium and barium, with magnesium being most preferred. While any counter anion is suitable in the catalyst of this invention, such as bromide, chloride and fluoride, the halides are preferred, with chloride being most preferred. Other suitable anions are nitrates, sulfate, phosphate, acetates, oxalate and cyanides.

The Group IA metal preferably constitutes from about 15 to about 45 weight percent of the total salt, more preferably from about 20 to about 30 weight percent of the total catalyst. The molar ratio of Group IIA or IIB metal:Group IA metal is suitably in the range from about 10:1 to 0.1:1, and preferably ranges from about 1.1:1 to about 0.9:1. Most preferably, the amount of Group IIA or IIB metal in the salt is suitably that amount which is about equimolar to that of Group IA. The Group IIA or IIB metal is preferably present in an amount ranging from about 4 to about 25 weight percent of the total catalyst, more preferably from about 4 to about 10 weight percent of the total catalyst. The amount of counter anion is that which is sufficient to neutralize the cations of the salt. The counter anion is preferably present in an amount ranging from about 10 to about 35 weight percent of the total catalyst, preferably from about 15 to about 25 weight percent.

Any support which will withstand the dehydrohalogenation conditions described herein can be used in the process of the present invention. Examples of appropriate supports include the well-known carbon supports such as activated carbon, carbon black, chars and coke. Other suitable supports that may be used to support the catalyst include pumice, silica gel, asbestos, diatomaceous earth, fullers earth, alumina, titania, zirconia, silica-alumina, magnesia, magnesium silicate, silicon carbide, silicalite and silica. Preferred supports include alumina and silica, with silica being the most preferred. A silica having a surface area between 25 m²/g and 300 m²/g, more preferably between 100 m²/g and 300 m²/g, and a pore volume in the range of 0.75 cc/g to 1.4 cc/g is particularly active in the process of the present invention.

The salt is suitably supported on the carrier material by any standard impregnation technique such as that disclosed in *Experimental Methods in Catalytic Research*, Vol. II, edited by R. B. Anderson and P. T. Dawson, Academic Press, New York, 1978. A solution of both the Group IA and Group IIA or IIB metal ions and the associated anions may be employed to impregnate the support material or salts of the Group IA and Group IIA or IIB cations may be impregnated from separate solutions. The resulting catalyst comprising the catalytically active salt and the support preferably comprises from about 1 to about 50 weight percent of the salt, with from about 20 to about 30 weight percent of the salt being most preferred.

In its second aspect (hereafter referred to as the dehydrohalogenation step), the process of the present invention comprises contacting a halogenated hydrocarbon or alkylene halohydrin with a Group IA metal halide, and a Group IIA or IIB metal oxide or metal hydroxide, together supported on a porous carrier material, under reaction conditions sufficient to form a reaction product comprising a corresponding unsaturated halohydrocarbon, unsaturated hydrocarbon, or alkylene oxide.

In one preferred embodiment, the reaction product further comprises a Group IIA or IIB metal halide, and the process further comprises the simultaneous step of contacting the Group IIA or IIB metal halide with a regenerant comprising an alkanol or water under reaction conditions sufficient to form a Group IIA or IIB metal oxide or metal hydroxide (hereafter referred to as the alkanol or water regeneration step).

In a second preferred embodiment, the reaction product further comprises a Group IIA or IIB metal hydroxy halide, and the process further comprises the simultaneous step of heating the Group IIA or IIB metal hydroxy halide under reaction conditions sufficient to form a Group IIA or IIB metal oxide or metal hydroxide (hereafter referred to as the heat regeneration step).

The halogenated hydrocarbons or alkylene halohydrins of the present invention may be aliphatic, cyclic, saturated, unsaturated or aromatic. The halogenated hydrocarbons or alkylene halohydrins of the present invention all contain in an aliphatic or alicyclic portion of the molecule the radical:

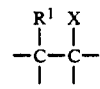

wherein X is chloro, bromo, iodo or fluoro, preferably chloro, and $R^1$ is a hydrogen or hydroxy group. Examples of such halohydrocarbons and halohydrins include 1,1,1-trichloroethane, 1,1,2-trichloroethane, 1,1-dichloroethane, 1,2-dichloroethane, 1,2-dichloropropane, 1,2,3-trichloropropane, 1,1,1-tribromoethane, α-chlorostyrene, 1,1,1-trifluoroethane, 1-chloro-2-propanol, and 1,1,1-trifluorochloroethane. Of these halohydrocarbons and halohydrins, 1,1,2-trichloroethane, 1,2-dichloropropane, 1-chloro-2-propanol, 2-chloro-1-propanol, and 1,2,3-trichloropropane are preferred, with 1-chloro-2-propanol, 2-chloro-1-propanol, and 1,1,2--trichloroethane being more preferred, and with 1,1,2--trichloroethane being most preferred.

Preferable Group IA metals employed in the processes of the invention include potassium, rubidium and cesium, with cesium being most preferred. Preferable halides include bromide, chloride and fluoride, with chloride being most preferred. Cesium chloride is the most preferred Group IA metal halide for its strong catalytic activity in dehydrohalogenation processes. Proposed equivalents for Group IA metal halides include any catalytic Group II, IV, V, VI, and VII metal halide capable of being stabilized in catalytic processes by basic substances. The Group IIA or IIB metals are preferably Group IIA metals, more preferably are magnesium, calcium, strontium and barium, with magnesium being most preferred. Magnesium oxide is the most preferred metal oxide for its strong basicity and its facile interconversion with the metal halide. Magnesium hydroxide is the most preferred metal hydroxide for its strong basicity. Proposed equivalents for Groups IIA or IIB metal oxides or metal hydroxides include any solid substances with a high base strength.

Any alkanol can be utilized in the alkanol regeneration step that will allow the regeneration process described herein to proceed. Typical alkanols useful for the present invention include methanol, ethanol, propanol, isopropanol, butanol, sec-butanol, tert-butanol and pentanol with methanol and ethanol being preferred. The most preferred alkanol in the process of the present invention is methanol. The molar ratio of alkanol or water to Group IIA or IIB metal halide in the alkanol or water regeneration process is in the range from 100:1 to about 1:100. The preferred ratio is in the range from about 10:1 to about 1:10, with the most preferred ratio being about 1:1.

The dehydrohalogenation step of the invention may be carried out at any temperature at which dehydrohalogenation of the halogenated hydrocarbon or alkylene halohydrin will occur. Suitable temperatures are in the range from about 80° C. to about 400° C., with between about 100° C. and about 325° C. being preferred. The reaction can be carried out at any pressure, super- or subatmospheric, which will not interfere with the dehydrohalogenation step. Typical pressures employed in the present invention are in the range from about 1 psia to about 300 psia. Preferably, the pressure is in the range from about 5 psia to about 100 psia.

The alkanol or water regeneration step may be carried out at any temperature at which reaction of the Group IIA or IIB metal halide to form a Group IIA or IIB metal oxide or metal hydroxide will occur and which does not substantially interfere with the catalytic productivity of the Group IA metal halide in the dehydrohalogenation step. Suitable temperatures which may be employed in the second and third aspects of the invention are in the range from about 100° C. to about 600° C., with between about 275° C. and about 525° C. being preferred. When alkanol is used as the regenerant, the most preferred temperature is between about 325° C. and about 350° C. When water is used as the regenerant, the most preferred temperature is between about 425° C. and about 525° C. The reaction can be carried out at any pressure which does not interfere with the regeneration step reactions or with catalytic productivity of the Group IA metal halide in the dehydrohalogenation step process. Typical pressures employed in the present invention are in the range from about 0 psia to about 300 psia. Preferably, the pressure is in the range from about 5 psia to about 100 psia.

The heat regeneration step may be carried out at any temperature at which reaction of the Group IIA or IIB metal hydroxy halide to form a Group IIA or IIB metal oxide or metal hydroxide and a hydrogen halide will occur and which does not interfere with the catalytic productivity of the Group IA metal halide in the dehydrohalogenation step process. Suitable temperatures which may be employed in the heat regeneration step of the invention are in the range from about 300° C. to about 600° C., with between about 400° C. and about 550° C. being preferred. The heat regeneration step can be carried out at any pressure, super- or subatmospheric, which does not interfere with the regeneration step or with the catalytic productivity of the Group IA metal halide in the dehydrohalogenation step process. Typical pressures employed in the present invention are in the range from about 0 psia to about 300 psia. Preferably the pressure is in the range from about 5 psia to about 100 psia.

The choice of regenerant to be used in the process of the invention will depend on the products formed in the dehydrohalogenation step. Metal halides formed in the dehydrohalogenation step may be contacted with an alkanol or water to regenerate the metal oxide or metal hydroxide. Metal hydroxy halides formed in the dehydrohalogenation step may be heated to regenerate the metal oxide or metal hydroxide. Advantageously, the products formed in the dehydrohalogenation step will depend on the working capacity of the Group IIA or IIB metal oxide or hydroxide to react with the saturated halohydrocarbon or halohydrin in the reaction mixture. For example, if only half of the available capacity of the Group IIA or IIB metal oxide or hydroxide is utilized, metal hydroxy halides are advantageously formed in the dehydrohalogenation process. If more than half of the available capacity of the Group IIA or IIB metal oxide or hydroxide is utilized, metal halides are advantageously formed. The working capacity of the catalyst of the invention may be determined by titration with HCl.

When the catalyst of this invention is to be used in the processes of this invention, it is preferable to initiate the process of the invention by performing the regeneration step first, in order to generate a Group IIA or IIB metal oxide or metal hydroxide.

In one preferred embodiment of the alkanol regeneration process, the two steps of the process are carried out simultaneously in the same reaction vessel. In the practice of this embodiment, the halohydrocarbon or halohydrin is dehydrochlorinated by contacting a vaporous feed of the halohydrocarbon or halohydrin with the catalyst at elevated temperature and atmospheric pressure to superatmospheric pressure for a time sufficient to effect the desired degree of conversion of the halohydrocarbon or halohydrin. The vaporous feed is preferably a mixture of the halohydrocarbon or halohydrin and the alcohol. While the invention is not to be bound by any mechanistic theory, the alcohol in this process is believed to serve as a hydroxide donor and a halide acceptor and thereby functions to regenerate the Group IIA or IIB metal halide to a Group IIA or IIB metal oxide or metal hydroxide and to recover the halide value as an alkyl halide. In the vapor phase, the presence of from about 2 to about 5 weight percent oxygen in the reactant feed stream serves to extend the life of the catalyst to more than 200 hours. The oxygen preferably comprises from about 0.01 to about 1.0 weight percent of the entire vaporous feed. The contact time of the vaporous mixture with the catalyst in the reactor is generally not more than about 3 minutes, preferably not more than about 30 seconds. Suitable superficial gas hourly space velocities (GHSV) for the vaporous feed are those which effect the desired conversion and selectivities. Preferably such GHSV is in the range from about 100 to about 10,000 hours$^{-1}$, most preferably from about 300 to about 3,000 hours$^{-1}$. The catalyst can be employed in the form of a packed bed or a fluidized bed.

This alkanol regeneration process embodiment may be carried out at any temperature which will allow both steps of the process to occur. Suitable temperatures are in the range from about 25° C. to about 475° C., with between about 275° C. and about 375° C. being preferred. This process may be carried out at any pressure which does not interfere with either reaction step. Typical pressures employed in the present invention are in the range from about 0 psia to about 500 psia. Preferably, the pressure is in the range from about 35 psia to about 100 psia.

In a second preferred embodiment of this invention, the steps of the alkanol, water, or heat regeneration processes are carried out in separate vessels, with means of introducing the reactants into the process, and means of separating out the reaction products and by-products. Suitable types of process equipment which may be used to perform the dehydrohalogenation step of the process of the invention include, for example, fixed, moving or fluidized bed catalytic reactors as described, for example, in P. Trambouze et al., *Chemical Reactors*, Editions Technip, Paris, pp. 369–377 (1988), incorporated herein by reference. In one embodiment, a series of fixed bed reactors may be employed with means for alternating the dehydrohalogenation and regeneration steps among the reactors. In a second embodiment, the process equipment additionally comprises means of transferring the Group IIA or IIB metal halide and Group IIA or IIB metal oxide or metal hydroxide between the vessels.

In the most preferred embodiment of the processes of the invention, the processes are carried out in a recirculating fluid bed reactor as illustrated, for example, in Venuto, P. B. and E. T. Habib, "Catalyst-Feedstock-Engineering Interactions in Fluid Catalytic Cracking", *Catal. Rev.-Sci. Eng.*, 18(1), pp. 15–22 (1978) and U.S. Pat. No. 4,309,279, incorporated herein by reference. This type of reactor comprises a riser section, a separator section, and a regenerator section, which are connected by means for sequentially cycling the reactants and products through the sections. The riser and regenerator sections additionally comprise means of introducing additional reactants and catalyst therein.

In the dehydrohalogenation step, halogenated hydrocarbons or alkylene halohydrins and catalytic materials are introduced into the riser section, wherein the dehydrohalogenation step of the process takes place. The riser section is connected to a separator section, wherein the unsaturated products and other by-products of the process, such as hydrogen chloride or methyl chloride, are separated from the solid catalytic materials. Preferably, the separator comprises a cyclone which is especially suitable for separating solid materials from gases. The separator is further connected to a regeneration section, wherein the regeneration step takes place. During the regeneration step in the alkanol or water regeneration process, an alkanol or water is introduced into the regeneration section, and is reacted with the solid catalytic materials. The regeneration section is further connected to the riser section to effect catalyst transfer, wherein additional saturated hydrocarbons or alkylene halohydrins may be introduced.

In an especially preferred embodiment of the invention, 1,1,2-trichloroethane is converted to vinylidene chloride in yields greater than 80 percent, most preferably greater than 90 percent, with less than 20 percent, most preferably less than 10 percent of cis-and trans-1,2-dichloroethane being formed.

SPECIFIC EMBODIMENTS

The following examples are included for illustrative purposes only and are not intended to limit the scope of the claims. All parts and percentages are by weight unless otherwise indicated.

Catalyst Preparation

To 13.97 g (0.083 mole) of CsCl is added 16.85 g (0.083 mole) of $MgCl_2 6H_2O$. The mixture is dissolved in 52 ml of water. The solution is then added to 20.0 g of $SiO_2$ (particle size 0.59–1.17 mm, surface area 185 m²/g, pore volume 1.4 cc/g) and air dried at 120° C. for 24 hours. The catalyst comprises 26.28 percent of Cs, 21.15 percent of Cl, 4.76 percent of Mg and a remaining percentage of silica.

EXAMPLE 1

A Hastalloy B tubular reactor (30.5 cm × 1.27 cm) containing 9.45 g (15.0 cc) of $CsMgCl_3 6H_2O$ supported on silica gel is heated to 425° C. and a mixture of 2.07 percent $O_2$ in $N_2$ saturated with $H_2O$ at 25° C. is passed through the reactor at a flow rate of 50 cc/min for 2 hours. A 50 cc/min flow rate of anhydrous 2.07 percent $O_2$ in $N_2$ is established in the reactor and the temperature of the reactor is decreased to 325° C. A premixed solution of 101.43 ml of methanol and 211.17 ml of 1,1,2-trichloroethane is introduced into the reactor at a flow rate of 10 ml/hr for 200 hours. The downstream product lines are heated to 180° C. to maintain the system in the vapor phase and the reactor effluent is analyzed periodically by gas chromatography. The effluent gases are condensed at −78° C. with a dry ice trap and the remaining volatiles are scrubbed with a 6N NaOH solution and vented.

EXAMPLES 2–8

Several catalysts are prepared in accordance with the method of Example 1. The catalysts are subjected to the same methanol/trichloroethane treatment as described in Example 1. The catalysts and their respective results are shown in Table I.

TABLE I

| Sample No. | Catalyst[1] | Selectivity[2] VC[4] | Cis-1,2 DCE[4] | Trans-1,2 DCE[4] | % Conversion[3] |
|---|---|---|---|---|---|
| 1 | $CsMgCl_3$ | 80.1 | 11.5 | 10.2 | 88.6 |
| 2 | $CsBaCl_3$ | 85.0 | 6.9 | 8.0 | 50.3 |
| 3 | $Cs(Ca,Mg)Cl_3$ | 79.4 | 9.7 | 10.9 | 84.3 |
| 4 | $Cs(Ba,Mg)Cl_3$ | 81.7 | 8.1 | 10.1 | 89.5 |
| 5 | $Cs_2MgCl_4$ | 65.6 | 14.2 | 14.1 | 81.2 |
| 6 | $CsMgFCl_2$ | 67.1 | 18.1 | 15.4 | 99.4 |
| $C_1$* | $MgCl_2$ | 8.3 | 13.2 | 78.4 | 34.4 |
| $C_2$* | CsCl | 67.0 | 10.6 | 22.3 | 7.5 |

[1] All salts supported on silica gel at a total salt concentration in the catalyst of about 50 percent.
[2] Selectivity is based on weight of vinylidene chloride produced divided by the weight of trichloroethane consumed.
[3] % Conversion = % of 1,1,2-trichloroethane converted to products
[4] VC is Vinylidene chloride and DCE is Dichloroethylene
*Not an example of the invention.

As evidenced by the data in Table I, the use of a mixed salt catalyst as in Sample Nos. 1–6 produces the desired vinylidene chloride in greater selectivities than do the single salt catalysts of Sample Nos. $C_1$ and $C_2$.

EXAMPLE 9

Dehydrochlorination of 1,1,2-Trichloroethane at 135° C.

A 0.285-g sample of 20 percent $CsMgCl_3/SiO_2$ contained in a 4-mm internal diameter tubular quartz reactor is treated at 325° C. with methanol to convert the $MgCl_2$ to MgO or $Mg(OH)_2$. The effluent is monitored continuously by mass spectroscopy for the evolution of methyl chloride. Upon cessation of methyl chloride production, the reactor is cooled to 135° C. and pulses of helium saturated with 1,1,2-trichloroethane at 25° C. are injected into the reactor via a gas sampling valve fitted with a 0.5-cc sample loop. The residence time of the reactants within the catalyst bed is 1.0 second. The reaction products are monitored via gas chromatography and give the following selectivities and conversions to vinylidene chloride as a function of pulse number. The remainder of the products are the cis and trans isomers of 1,2-dichloroethane at a ratio of 0.66:1. A small amount of chloroacetylene is observed during the initial 1-3 pulses.

| Pulse | Conversion | Selectivity |
|-------|------------|-------------|
| 1     | 100        | 83.3        |
| 2     | 100        | 86.2        |
| 3     | 100        | 87.3        |
| 4     | 100        | 87.7        |
| 5     | 96.4       | 87.7        |
| 17    | 55.9       | 88.3        |

The conversion decreases linearly from pulse 6–17 with the selectivity to vinylidene chloride remaining constant in the range of 87–88 percent. The total amount of 1,1,2-trichloroethane reacted is 0.5 mg.

EXAMPLE 10

Dehydrochlorination of 1,1,2-trichloroethane at 280° C.

Using the same setup as in Example 9, helium saturated with 1,1,2-trichloroethane is injected into a reactor maintained at 280° C. The selectivity to vinylidene chloride is constant at 86–87 percent with conversions in the range of 90–70 percent over 50 pulses.

What is claimed is:

1. A dehydrohalogenation catalyst in the form of a compound comprising a Group IA metal cation, a Group IIA or IIB metal cation and a neutralizing number of at least one counter anion on a porous carrier material, wherein the molar ratio of Group IIA or IIB metal:Group IA metal is in the range of from about 10:1 to about 0.1:1.

2. The catalyst of claim 1 wherein the Group IA metal is potassium or cesium.

3. The catalyst of claim 2 wherein the Group IA metal is cesium.

4. The catalyst of claim 1 wherein the Group IIA or IIB metal is magnesium, calcium, strontium or barium.

5. The catalyst of claim 4 wherein the Group IIA or IIB metal is magnesium.

6. The catalyst of claim 1 wherein the counter anion(s) is chloride.

7. The catalyst of claim 6 wherein the porous carrier material is silica, alumina or activated carbon.

8. The catalyst of claim 7 wherein the porous carrier material is silica.

* * * * *